(12) United States Patent
Parsonage

(10) Patent No.: US 9,861,436 B2
(45) Date of Patent: Jan. 9, 2018

(54) ABLATION CATHETERS AND SYSTEMS INCLUDING ROTATIONAL MONITORING MEANS

(71) Applicant: St. Jude Medical, Cardiology Division, Inc., St. Paul, MN (US)

(72) Inventor: Edward E. Parsonage, St. Paul, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 0 days.

(21) Appl. No.: 15/334,686

(22) Filed: Oct. 26, 2016

(65) Prior Publication Data

US 2017/0042611 A1 Feb. 16, 2017

Related U.S. Application Data

(63) Continuation of application No. 13/799,623, filed on Mar. 13, 2013, now Pat. No. 9,510,902.

(51) Int. Cl.
*A61B 18/14* (2006.01)
*A61B 18/00* (2006.01)
*A61B 90/00* (2016.01)

(52) U.S. Cl.
CPC .......... *A61B 18/1492* (2013.01); *A61B 90/06* (2016.02); *A61B 90/08* (2016.02);
(Continued)

(58) Field of Classification Search
CPC ............................. A61B 19/46; A61B 18/1492
See application file for complete search history.

(56) References Cited

U.S. PATENT DOCUMENTS

| 3,650,277 A | 3/1972 | Sjostrand et al. |
| 4,658,819 A | 4/1987 | Harris et al. |

(Continued)

FOREIGN PATENT DOCUMENTS

| WO | 97/45157 | 12/1997 |
| WO | 00/66020 | 11/2000 |

(Continued)

OTHER PUBLICATIONS

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.

(Continued)

*Primary Examiner* — Alyssa M Alter
(74) *Attorney, Agent, or Firm* — Armstrong Teasdale LLP

(57) ABSTRACT

The present disclosure provides an improved ablation catheter. In particular, the present disclosure provides an improved renal denervation ablation catheter and system including a catheter handle and a means for tracking, monitoring, and/or recording the circumferential angular history of the renal denervation ablation catheter handle. The renal denervation ablation catheters in accordance with the present disclosure are well-suited for use with a renal denervation ablation system that can record the circumferential angular history of the renal denervation catheter handle, and hence the circumferential angular ablation history of the catheter electrode within a vessel, and use this data in combination with other known information to estimate the percent circumferential denervation of the vessel.

20 Claims, 4 Drawing Sheets

(52) U.S. Cl.
CPC ............ *A61B 2018/00202* (2013.01); *A61B 2018/00404* (2013.01); *A61B 2018/00434* (2013.01); *A61B 2018/00511* (2013.01); *A61B 2018/00577* (2013.01); *A61B 2090/067* (2016.02); *A61B 2090/0811* (2016.02)

(56) References Cited

U.S. PATENT DOCUMENTS

| | | |
|---|---|---|
| 5,035,694 A | 7/1991 | Kasprzyk et al. |
| 5,255,679 A | 10/1993 | Imran |
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,044 B1 | 4/2001 | Kordis |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hedge et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 9,022,948 B2 | 5/2015 | Wang |
| 9,439,598 B2 | 9/2016 | Shimada et al. |
| 9,510,902 B2 * | 12/2016 | Parsonage .......... A61B 18/1492 |
| 2002/0068885 A1 | 6/2002 | Harhen et al. |
| 2002/0120304 A1 | 8/2002 | Mest |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0288730 A1 | 12/2005 | Deem et al. |
| 2006/0089678 A1 | 4/2006 | Shalev |
| 2007/0135875 A1 | 6/2007 | Demarais et al. |
| 2008/0255478 A1 | 10/2008 | Burdette |
| 2009/0076409 A1 | 3/2009 | Wu et al. |
| 2009/0131933 A1 * | 5/2009 | Ghabrial ............ A61B 18/1445 606/51 |
| 2010/0016762 A1 | 1/2010 | Thapliyal et al. |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2011/0004087 A1 | 1/2011 | Fish et al. |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0218550 A1 * | 9/2011 | Ma ................... A61B 17/07207 606/130 |
| 2011/0257641 A1 | 10/2011 | Hastings et al. |
| 2011/0264011 A1 | 10/2011 | Wu et al. |
| 2011/0264086 A1 | 10/2011 | Ingle |
| 2012/0143097 A1 | 6/2012 | Pike, Jr. |
| 2012/0143298 A1 | 6/2012 | Just et al. |
| 2012/0296232 A1 | 11/2012 | Ng |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

Janssen, Ben J.A. et al, Renal Nerves in Hypertension, Miner Electrolyte Metab 1989;15:74-82.

Jin, Yu et al, No Support for Renal Denervation in a Meta-Analysis, JACC vol. 62, No. 21, 2013 Correspondence Nov. 19/26, 2013:2029-30.

(56) References Cited

OTHER PUBLICATIONS

Kaltenbach, Benjamin et al, Renal Artery Stenosis After Renal Sympathetic Denervation, J Am Coll Cardiol. Dec. 25, 2012;60(25):2694-5.

Kaltenbach, Benjamin et al, Renal Sympathetic Denervation as Second-Line Therapy in Mild Resistant Hypertension: A Pilot Study, Catheterization and Cardiovascular Interventions 81:335-339; Feb. 2013.

Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.

Kandzari, David E. et al, Catheter-Based Renal Denervation for Resistant Hypertension: Rationale and Design of the Symplicity HTN-3 Trial, Clin. Cardiol. 35, 9, 528-535 (2012).

Kapural, Leonardo et al, Radiofrequency Ablation for Chronic Pain Control, Current Pain and Headache Reports 2001, 5:517-525.

Kassab, Salah et al, Renal Denervation Attenuates the Sodium Retention and Hypertension Associated with Obesity, Hypertension vol. 25, No. 4, Part 2 Apr. 1995.

Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.

Katholi, Richard E. et al, Role of the Renal Nerves in the Pathogenesis of One-Kidney Renal Hypertension in the Rat, Hypertension. 1981;3:404-409.

Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.

Katritsis, Demosthenes et al, Recurrence of Left Atrium-Pulmonary Vein Conduction Following Successful Disconnection in Asymptomatic Patients, Europace (2004) 6, 425e432.

Killip III, Thomas, Oscillation of Blood Flow and Vascular Resistance During Mayer Waves, Circulation Research, vol. XI, Dec. 1962, 987-993.

Kingwell, Bronwyn A. et al, Assessment of Gain of Tachycardia and Bradycardia Responses of Cardiac Baroreflex, Am J Physiol Heart Circ Physiol 260:H1254-H1263, 1991.

Kirchheim, H. et al, Sympathetic Modulation of Renal Hemodynamics, Renin Release and Sodium Excretion, Klin Wochenschr (1989) 67: 858-864.

Klein, GE et al, Endovascular Treatment of Renal Artery Aneurysms with Conventional Non-Detachable Microcoils and Guglielmi Detachable Coils, Br J Urol. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.

Krum, Henry et al, Device-Based Antihypertensive Therapy: Therapeutic Modulation of the Autonomic Nervous System, Circulation. 2011;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.

Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.

Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

Lambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luscher, Thomas F. et al, Renal Nerve Ablation After Symplicity HTN-3: Confused at the Higher Level?; European Heart Journal, doi:10.1093/eurheartj/ehu195; May 14, 2014.

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.

Mahfoud, Felix et al, Expert Consensus Document from the European Society of Cardiology on Catheter-Based Renal Denervation, European Heart Journal, Apr. 25, 2013; 34(28):2149-57.

Mancia, Giuseppe et al, Sympathetic Activation in the Pathogenesis of Hypertension and Progression of Organ Damage, Hypertension Journal of the American Heart Association, 1999, 34:724-728.

McGahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreet.com.

Medtronic, Inc. Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RDN Therapy with the Symplicity Renal Denervation System, Procedure Fact Sheet, www.medtronic.com, 2011.

Medtronic, Inc., Renal Denervation (RDN) Novel Catheter-based Treatment for Hypertension, Symplicity RDN System Common Q&A, 2011.

Medtronic, Inc., Scientific Basis Behind Renal Denervation for the Control of Hypertension, Dec. 2012, http://www.icimeeting.com/2012/images/stories/PDF/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.

Meredith, I T et al, Exercise Training Lowers Resting Renal but Not Cardiac Sympathetic Activity in Humans; Hypertension Journal of the American Heart Association, 1991;18:575-582.

Michaelis, Lawrence L. et al, Effects of Renal Denervation and Renin Depletion on the Renal Responses to Intravascular Volume Expansion, Ann Surg. Mar. 1972; 175(3): 424-430.

Millard, E.C. et al, Renal Embolization for Ablation of Function in Renal Failure and Hypertension, Postgraduate Medical Journal (1989) 65, 729-734.

Abboud, Francois M., The Sympathetic System in Hypertension, State-of-the-Art Review, Hypertension Journal of the American Heart Association, Hypertension 4 (suppl II): II-208-II-225, 1982.

(56) References Cited

OTHER PUBLICATIONS

Allen, Edgar V., Sympathectomy for Essential Hypertension, Circulation Journal of the American Heart Association, vol. VI, Jul. 1952, 131-140.

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

Ardian, Inc., Ardian(R) Receives 2010 EuroPCR Innovation Award and Demonstrates Further Durability of Renal Denervation Treatment for Hypertension, PR Newswire, Jun. 3, 2010.

Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.

Badoer, Emilio et al, Cardiac Afferents Play the Dominant Role in Renal Nerve Inhibition Elicited by Volume Expansion in the Rabbit, American Journal of Physiology, 1998, R383-R388.

Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.

Bao, Gang et al, Blood Pressure Response to Chronic Episodic Hypoxia: Role of the Sympathetic Nervous System, American Journal of Physiology, 1997, 95-101.

Barajas, Luciano et al, Anatomy of the Renal Innervation: Intrarenal Aspects and Ganglia of Origin, Canadian Journal of Physiology and Pharmacology, vol. 70, No. 5, May 1992, 735-749.

Barajas, Luciano et al, Monoaminergic Innervation of the Rat Kidney: A Quantitative Study, American Journal of Physiology, vol. 259, No. 3, Sep. 1990, F503-F511.

Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.

Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.

Bello-Reuss, Elsa et al, Effects of Acute Unilateral Renal Denervation in the Rat, The Journal of Clinical Investigation, vol. 56, Jul. 1975, 208-217.

Benito, Fernando et al, Radiofrequency Catheter Ablation of Accessory Pathways in Infants, Heart, 1997, 78, 160-162.

Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.

Bertog, Stefan C. et al, Renal Denervation for Hypertension, JACC: Cardiovascular Interventions, vol. 5, No. 3, Mar. 2012, 249-258.

Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.

Blankestijn, Peter J. et al, Renal Denervation: Potential Impact on Hypertension in Kidney Disease?, Nephrol Dial Transplant (2011) 0: 1-3.

Blankestijn, Peter J. et al, Sympathetic Overactivity in Renal Failure Controlled by ACE Inhibition: Clinical Significance, Nephrol Dial Transplant, 2000, 15, 755-758.

Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.

Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.

Brookes, Linda et al, Renal Denervation: Is Reality Meeting Expectations?, An Interview with Michel Azizi, MD, PhD, Medscape, Jan. 7, 2013.

Bunte, Matthew C. et al, Endovascular Treatment of Resistant and Uncontrolled Hypertension, JACC: Cardiovascular Interventions, vol. 6, No. 1, Jan. 2013, 1-9.

Calleary, Hickey D. et al, Pre-Transplant Bilateral Native Nephrectomy for Medically Refractory Hypertension, The Irish Medical Journal, Jul.-Aug. 2001;94(7):214-6.

Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.

Campese, V.M., Is Hypertension in Chronic Renal Failure Neurogenic in Nature?, Nephrol Dial Transplant, 1994, 9: 741-742.

Campese, Vito M. et al, Neurogenic Factors in Renal Hypertension, Current Hypertension Reports, 2002 4: 256-260.

Campese, Vito M. et al, Renal Afferent Denervation Prevents Hypertension in Rats With Chronic Renal Failure, Hypertension, 1995, 25, 878-882.

Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.

Campese, Vito M., Interventional Hypertension: A New Hope or a New Hype? The Need to Redefine Resistant Hypertension, J Hypertens. Nov. 2013; 31(11):2118-21.

Canadian Agency for Drugs and Technologies in Health, Catheter-Based Renal Denervation for Treatment-Resistant Hypertension; Issues in Emerging Health Technologies, Issue 121, Mar. 2013.

Carlstedt, Thomas et al, Regrowth of Lesioned Dorsal Root Nerve Fibers into the Spinal Cord of Neonatal Rats, Neuroscience Letters Feb. 10, 1987;74(1):14-8.

Chabanier, H. et al, On the Decapsulation and Neurectomy of the Kidnesy in Permanent Hypertensive States, The Medical Press, Feb. 22, 1936, No. 16, 307-310.

Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.

Ciriello, John et al, Renal Afferents and Hypertension, Current Hypertension Reports 2002, 4:136-142.

Converse, Richard L. et al, Sympathetic Overactivity in Patients with Chronic Renal Failure, The New England Journal of Medicine, vol. 327, No. 27, 1992, 1912-1918.

Crile, George, The Clinical Results of Celiac Ganglionectomy in the Treatment of Essential Hypertension, Annals of Surgery, Jun. 1938; 107(6): 909-916.

Cruickshank, J.M., Beta-Blockers Continue to Surprise Us, European Heart Journal (2000) 21, 354-364.

Curtis, John J. et al, Surgical Therapy for Persistent Hypertension After Renal Transplantation, Transplantation, vol. 31, No. 2, 1981, 125-128.

Dailey, U.G., Surgical Treatment of Hypertension: A Review—Part II, Journal of the National Medical Association, May 1948, vol. 40, No. 3., 113-116.

Dailey, U.G., Surgical Treatment of Hypertension: A Review—Part III, Journal of the National Medical Association, Jul. 1948, vol. 40, No. 4, 160-162.

Dailey, U.G., The Surgical Treatment of Hypertension: A Review, Journal of the National Medical Association, Mar. 1948, vol. 40, No. 2, 76-79.

Davis, Mark I. et al, Effectiveness of Renal Denervation Therapy for Resistant Hypertension a Systematic Review and Meta-Analysis, Journal of the American College of Cardiology, vol. 62, No. 3, Jul. 16, 2013, 231-241.

De Wardener, H.E., The Hypothalamus and Hypertension, Physiological Reviews,vol. 81, No. 4, Oct. 2001.

Dequattro V. et al, The Sympathetic Nervous System: The Muse of Primary Hypertension, Journal of Human Hypertension, 2002, 16 (Suppl 1), S64-S69.

Dibona, Gerald F. et al, Neural Control of Renal Function, Physiological Reviews, vol. 77, No. 1, Jan. 1997, 75-197.

(56) References Cited

OTHER PUBLICATIONS

Dibona, Gerald F. et al, Translational Medicine: The Antihypertensive Effect of Renal Denervation, Americal Journal of Physiology, 2010, 298, R245-R253.

Dibona, Gerald F., Neural Control of Renal Function: Cardiovascular Implications, Hypertension Journal of the American Heart Association, vol. 13, No. 6, Part 1, Jun. 1989, 539-548.

Dibona, Gerald F., Neural Control of the Kidney: Functionally Specific Renal Sympathetic Nerve Fibers, American Journal of Physiology, 2000, 279, R1517-R1524.

Dibona, Gerald F., Neural Control of the Kidney: Past, Present, and Future, Hypertension Journal of the American Heart Association, vol. 41, Mar. 2003, Part II, 621-624.

Robbins, Ivan M. et al, Pulmonary Vein Stenosis After Catheter Ablation of Atrial Fibrillation, Circulation Journal of the American Heart Association, 1998;98:1769-1775.

Rocha-Singh, Krishna J., Catheter-Based Sympathetic Renal Denervation a Novel Strategy for the Treatment of Resistant Hypertension, Endovascular Today, Aug. 2009, 52-56.

Rocha-Singh, Krishna J., Renal Artery Denervation: A Brave New Frontier, Endovascular Today, Feb. 2012, 45-53.

Sanderson, John E. et al, Effect of B-Blockade on Baroreceptor and Autonomic Function in Heart Failure, Clinical Science (1999) 96, 137-146.

Santos, Mario et al, Renal Sympathetic Denervation in Resistant Hypertension, World J Cardiol Apr. 26, 2013; 5(4): 94-101.

Savard, Sebastien et al, Eligibility for Renal Denervation in Patients With Resistant Hypertension When Enthusiasm Meets Reality in Real-Life Patients, J Am Coll Cardiol. 2012;60(23):2422-2424.

Schauerte, Patrick et al, Catheter Ablation of Cardiac Autonomic Nerves for Prevention of Vagal Atrial Fibrillation, Circulation Journal of the American Heart Association, 2000, 102:2774-2780.

Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.

Schlaich, Markus P. et al, Renal Denervation as a Therapeutic Approach for Hypertension Novel Implications for an Old Concept, Hypertension Journal of the American Heart Association, 2009;54:1195-1201.

Schlaich, Markus P. et al, Renal Sympathetic-Nerve Ablation for Uncontrolled Hypertension, The New England Journal of Medicine, 2009; 361:932-934.

Schmieder, Roland E. et al, ESH Position Paper: Renal Denervation—An Iterventional Therapy of Resistant Hypertension, Journal of Hypertension, 2012, 30:837-841.

Schmieder, Roland E. et al, Updated EHS Position Paper on Interventional Therapy of Resistant Hypertension, EuroIntervention, May 2013; 9:R58-R66.

Sellers, Alfred M. et al, Adrenalectomy and Sympathectomy for Hypertension Ten Year Survival, Archives of Surgery, vol. 89, Nov. 1964, 880-886.

Sen, S.K., Some Observations on Decapsulation and Denervation of the Kidney, The British Journal of Urology, vol. 8, Issue 4, Dec. 1936, 319-328.

Shiraki, Iwao William, Correction of Renal Hypertension by Ligation of Stenotic Segmental Renal Artery, Urology, vol. IX, No. 3, Mar. 1977, 296-298.

Shonai, Takaharu et al, Renal Artery Aneurysm: Evaluation with Color Doppler Ultrasonography Before and After Percutaneous Transarterial Embolization, J Ultrasound Med 19:277-280, 2000.

Silver, Donald et al, Renovascular Hypertension From Renal Artery Compression by Congenital Bands, Annals of Surgery, Feb. 1976, 161-166.

Smith, Gardner W. et al, Surgical Results and the Diagnostic Evaluation of Renovascular Hypertension, Annals of Surgery, May 1968, 669-680.

Smith, Harold P. et al, Radiofrequency Neurolysis in a Clinical Model Neuropathological Correlation, J Neurosurg 55:246-253, 1981.

Smithwick, R.H., An Evaluation of the Surgical Treatment of Hypertension, The Bulletin, Nov. 1949; 25(11):698-716.

Smithwick, Reginald H. et al, Splanchnicectomy for Essential Hypertension, The Journal of the American Medical Association, vol. 152, No. 16, Aug. 1953, 1501-1504.

Solis-Herruzo, J.A. et al, Effects of Lumbar Sympathetic Block on Kidney Function in Cirrhotic Patients with Hepatorenal Syndrome, Journal of Hepatology, 1987; 5: 167-173.

Sowers, James R. et al, Diabetes, Hypertension, and Cardiovascular Disease: An Update, Hypertension Journal of The American Heart Association, 2001;37:1053-1059.

Stanley, James C., Surgical Treatment of Renovascular Hypertension, The American Journal of Surgery, vol. 174, Aug. 1997, 102-110.

Stella, Andrea et al, Effects of Reversible Renal Denervation on Haemodynamic and Excretory Functions of the Ipsilateral and Contralateral Kidney in the Cat, Journal of Hypertension 1986, 4: 181-188.

Stuart, Candace, Newest Frontier in Cardiac Care: Kidneys; Cardiovascular Business, Dec. 13, 2012.

Stuart, Mary, Masterminds of Ardian: An Interview With Inventors Mark Gelfand and Howard Levin, Windhover Information, Start-Up Jan. 1, 2011.

Sun, Yingxian et al, Risk of Coronary Stenosis with Venous Ablation for Epicardial Accessory Pathways, PACE, Apr. 2001, Part II, vol. 24, 605.

Swartz, John F. et al, Radiofrequency Endocardial Catheter Ablation of Accessory Atrioventricular Pathway Atrial Insertion Sites, Circulation Journal of The American Heart Association, 1993;87:487-499.

Teigen, Corey L. et al, Segmental Renal Artery Embolization for Treatment of Pediatric Renovascular Hypertension, Journal of Vascular and Interventional Radiology, 1992; 3:111-117.

Teixeira, Maria Do Carmo et al, 1992; Role of the Peripheral Renin Profile in Predicting Blood Pressure Control After Bilateral Nephrectomy in Renal-Transplanted Patients, Nephrol Dial Transplant (1998) 13: 2092-2097.

Teo, W S et al, Radiofrequency Catheter Ablation of Accessory Pathways: The Initial Experience in Singapore, Singapore Medical Journal, 1994; vol. 35:36-40.

Thiebot, J. et al, Bilateral Nephrectomy by Embolization of the Renal Arteries: A Report on Five Cases (author's transl), Sem Hop. Apr. 8-15, 1980;56(13-14):670-5.

Thomas, George et al, Renal Denervation to Treat Resistant Hypertension: Guarded Optimism, Cleveland Clinic Journal of Medicine, vol. 79, No. 7, Jul. 2012, 501-510.

Thomas, Natalie A., Secondary Consideration in Nonobviousness Analysis: The Use of Objective Indicia Following *KSR V. Teleflex*, NYU Law Review, vol. 86, No. 6, Dec. 2011, 2070-2112.

Ting, Chih-Tai et al, Arterial Hemodynamics in Human Hypertension Effects of Angiotensin Converting Enzyme Inhibition, Hypertension Journal of The American Heart Association, 1993;22:839-846.

Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.

Valente, John F. et al, Laparoscopic Renal Denervation for Intractable ADPKD-Related Pain, Nephrol Dial Transplant (2001) 16:160.

Villarreal, Daniel et al, Effects of Renal Denervation on Postprandial Sodium Excretion in Experimental Heart Failure, American Journal of Physiology, May 1994;266(5 Pt 2):R1599-R1604.

Vonend, Oliver et al, Secondary Rise in Blood Pressure After Renal Denervation, The Lancet, vol. 380, Issue 9843, p. 778, Aug. 25, 2012.

Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.

Webb, R.L. et al, Functional Identification of the Central Projections of Afferent Renal Nerves, Clin. and Exper.—Theory and Practice, Ag(Suppl.I), 47-57 (1987).

(56) References Cited

OTHER PUBLICATIONS

Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Mazer, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Zazgornik, Jan et al, Bilateral Nephrectomy: The Best, but Often Overlooked, Treatment for Refractory Hypertension in Hemodialysis Patients, AJH 1998; 11:1364-1370.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, Jan. 28, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. Jul. 8, 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.

Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:I-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of The American Heart Association, vol. IV, Aug. 1951, 173-183.
Hoppe, UTA C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.

(56) References Cited

OTHER PUBLICATIONS

Howard, James P. et al, Size of Blood Pressure Reduction from Renal Denervation: Insights from Meta-Analysis of Antihypertensive Drug Trials of 4121 Patients with Focus on Trial Design: the Converge Report, Heart, Sep. 15, 2013; 0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, Nov. 8, 2013; 0: 1-8.
Huang Shoei K. Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of The American Heart Association, 1998;32:249-254.
Humpreys, Michael H., Renal Nerves and CKD: Is Renal Denervation the Answer?, Journal of The American Socity of Nephrology, 2012, 23: 1-3.
International Search Report and Written Opinion for Application No. PCT/US2010/054637 dated Jan. 3, 2011.
International Search Report and Written Opinion for Application No. PCT/US2010/054684 dated Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Izzo, Jr, Joseph L. et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013; Nov. 28, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; Mar. 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5 , pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.

(56) References Cited

OTHER PUBLICATIONS

Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.

Parati, Gianfranco et al, The Human Sympathetic Nervous System: Its Relevance in Hypertension and Heart Failure, European Heart Journal (2012) 33, 1058-1066.

Parmar, Arundhati, Analyst: Medtronic Will Likely Acquire Another Hypertension Therapy Firm, Medcity News, Apr. 27, 2012; 3:06 p.m.; medcitynews.com.

Pavlovich, Christian P. et al, Percutaneous Radio Requency Ablation of Small Renal Tumors: Initial Results; The Journal of Urology, vol. 167, Jan. 10-15, 2002.

Pearce, John A. et al, Blood Vessel Architectural Features and Their Effect on Thermal Phenomena, Critical Reviews, vol. CR75, , Bellingham, WA: SPIE Optical Engineering Press; 2000, p. 231-277.

Beet, Max Minor, Hypertension and Its Surgical Treatment by Bilateral Supradiaphragmatic Splanchnicectomy, American Journal of Surgery, vol. 75, Issue 1, Jan. 1948, 48-68.

Perry, C. Bruce, Malignant Hypertension Cured by Unilateral Nephrectomy, British Heart Journal, Jul. 1945; 7(3): 139-142.

Persu, Alexandre et al, Renal Denervation: Ultima Ratio or Standard in Treatment-Resistant Hypertension, Hypertension Journal of The American Heart Association, Sep. 2012;60(3):596-606.

Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.

Plouin, Pierre-Francois et al, Blood Pressure Outcome of Angioplasty in Atherosclerotic Renal Artery Stenosis a Randomized Trial, Hypertension Journal of The American Heart Association, 1998;31:823-829.

Poutasse, Eugene F., Surgical Treatment of Renal Hypertension, American Journal of Surgery, vol. 107, Jan. 1964, 97-103.

Pugsley, M.K. et al, The Vascular System an Overview of Structure and Function, Journal of Pharmacological and Toxicological Methods 44 (2000) 333-340.

Putney, John Paul, Are Secondary Considerations Still "Secondary"?:An Examination of Objective Indicia of Nonobviousness Five Years After KSR, Intellectual Property Brief, vol. 4, Issue 2, Article 5, 2012, 45-59.

Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.

Rippy, Marian K. et al, Catheter-Based Renal Sympathetic Denervation: Chronic Preclinical Evidence for Renal Artery Safety, Clin Res Cardiol (2011) 100:1095-1101.

Ritz, Eberhard, New Approaches to Pathogenesis and Management of Hypertension, Clin J Am Soc Nephrol 4: 1886-1891, 2009.

\* cited by examiner

ABLATION CATHETERS AND SYSTEMS INCLUDING ROTATIONAL MONITORING MEANS

CROSS-REFERENCE TO RELATED APPLICATIONS

This application is a continuation application of U.S. patent application Ser. No. 13/799,623, filed on Mar. 13, 2013, the entire contents and disclosure of which are hereby incorporated herein by reference in their entirety.

BACKGROUND OF THE DISCLOSURE a. Field of the Disclosure

The present disclosure generally relates to ablation catheters. In particular, the present disclosure relates to renal denervation ablation catheters and systems including a catheter handle and a means for tracking, recording, and/or monitoring the circumferential angular history of the renal denervation ablation catheter handle. The renal denervation ablation catheters in accordance with the present disclosure are well-suited for use with a renal denervation ablation system that can track and record the circumferential angular history of the renal denervation catheter handle, and hence the circumferential angular ablation history of the catheter electrode(s) within a vessel, and use this data in combination with other known information to estimate the percent circumferential denervation of the vessel.

b. Background Art

It is known that various ablation procedures for the ablation of perivascular renal nerves have been used for the treatment of hypertension, and specifically for drug-resistant hypertension. Generally, one or more radiofrequency electrodes are introduced into the body and fed into the renal artery and used to ablate the efferent and afferent nerves that generally run the length of the artery. In some cases, a single ablation procedure may include six to ten or more ablation areas along and around the wall of the artery. Typically, the doctor performing the procedure will ablate one discreet area of the artery and then pull the ablation electrode a desired distance lengthwise about the length of the artery and also rotate the handle of the catheter to move the ablation electrode circumferentially around the artery. In some cases, the doctor may move the ablation electrode circumferentially about 45 degrees around the artery wall between ablations. By varying the ablation treatment sites lengthwise down and circumferentially around the artery wall, the overall damage to the wall can be reduced or minimized while the overall ablation of the efferent and afferent nerves can still be substantially complete and effective.

During the ablation procedure, the doctor performing the procedure generally attempts to monitor and track all of the areas of the artery wall that have previously been ablated to avoid over-treatment of any one site. This monitoring and tracking should be done both along the length of the artery as well as around the circumference of the artery wall to ensure proper ablation of the arterial nerves and the best procedural results.

Based on the foregoing, it would be advantageous to provide a circumferential angle tracking device for tracking and recording the rotational history of a renal denervation catheter handle, and hence a renal denervation catheter electrode(s) directed thereby, to allow for more precise and thorough ablation of a renal artery and a reduced occurrence of artery damage due to over-ablation of a single spot. Additionally, it would be beneficial if the circumferential angle tracking device is easily integrateable with both single and multiple-electrode ablation catheter systems.

SUMMARY OF THE DISCLOSURE

It is desirable to be able to provide a means for tracking, monitoring, and/or recording the rotational history of an ablation catheter handle, and specifically a renal denervation ablation catheter handle, and hence the ablation electrode(s) directed thereby, to allow for a more complete circumferential artery ablation and improved procedural outcomes. It is also desirable to provide methods of using the means for tracking, monitoring, and/or recording the rotational ablation history of an ablation catheter and methods of estimating the overall percent denervation of renal efferent and afferent nerves. The present disclosure is directed to various means for tracking, monitoring, and/or recording the rotational history of an ablation catheter handle, and specifically a renal ablation catheter handle such that the circumferential angle is recorded for each ablation made by the electrode so that a more complete and accurate total ablation procedure may be performed. The embodiments disclosed herein are applicable to both single-electrode and multiple-electrode ablation systems. The present disclosure is also directed to methods of tracking, monitoring, and/or recording the angular circumferential ablation history of an ablation catheter, and to methods of estimating the circumferential percent renal denervation for a renal artery.

The present disclosure is directed to an ablation catheter system comprising a catheter handle, an elongate catheter body, an electrode, and a means for tracking a circumferential rotational history of the catheter handle.

The present disclosure is further directed to a method for tracking the circumferential ablation history of a renal artery. The method comprises ablating at least two areas on the renal artery using an ablation system comprising an ablation catheter comprising a catheter handle, an elongate catheter body, an electrode, and a means for tracking a circumferential rotational history of the catheter handle, and recording the circumferential rotational history of the catheter handle for each ablation.

The present disclosure is further directed to a method for estimating the circumferential percent renal denervation for a renal artery. The method comprises performing at least two ablations on the renal artery using an ablation system comprising an ablation catheter comprising a catheter handle, an elongate catheter body, an electrode, and a means for recording a circumferential rotational history of the catheter handle, recording a circumferential angle for each ablation, and using an average ablation spot size, a diameter of the artery, and circumferential angle for each ablation to estimate the circumferential percent renal denervation for the artery.

It has been found that the rotational angular ablation history of an ablation electrode, and specifically a renal ablation electrode, can be tracked, monitored and/or recorded precisely by using a rotational monitoring device in combination with the catheter handle that directs the ablation electrode inside of the artery. By monitoring, tracking and/or recording the rotational history of the catheter handle that directs or "steers" the ablation electrode within the artery, the ablation history of the electrode can be precisely tracked and recorded allowing for the percent denervation of the artery to be estimated and monitored during the renal denervation procedure. By more closely monitoring and controlling the ablation history of the ablation electrode, a more precise and thorough ablation of the nerves in the renal artery can be accomplished resulting in improved patient outcomes.

DETAILED DESCRIPTION OF THE DISCLOSURE

The ablation catheters, and specifically the renal denervation ablations catheters, and related methods of the present disclosure provide an improved ablation catheter that can easily and accurately track, record, and/or monitor the angular rotational history of the catheter, and specifically the catheter handle, during an ablation procedure, such as a renal denervation ablation procedure. This angular rotational history is directly related to the rotational ablation history of the catheter electrode located within the body such that an operator of the catheter system can accurately track and determine the circumferential ablation history of an artery or other area being treated. With this circumferential ablation history, the operator can more readily ascertain whether a complete circumferential ablation of an artery has been made, and can also use this circumferential ablation history along with other known information to accurately estimate the percent of denervation of renal efferent and afferent nerves. This can lead to improved patient outcomes and improved safety.

Embodiments of the present disclosure provide specific improvements to an ablation catheter, and specifically to an ablation catheter for use in a renal denervation procedure. The ablation catheters of the present disclosure include a means for tracking a circumferential rotational history of the catheter handle such that the circumferential rotational history of the ablation electrode directed by the catheter handle within an artery is accurately known. The rotational monitoring means for tracking the circumferential history of the catheter handle may include a non-rotating rotational monitor (relative to the catheter handle) appropriately marked with angular measurements and configured such that the catheter handle may rotate within, or may include electronic or other means for rotational monitoring as described herein.

Figure 1:
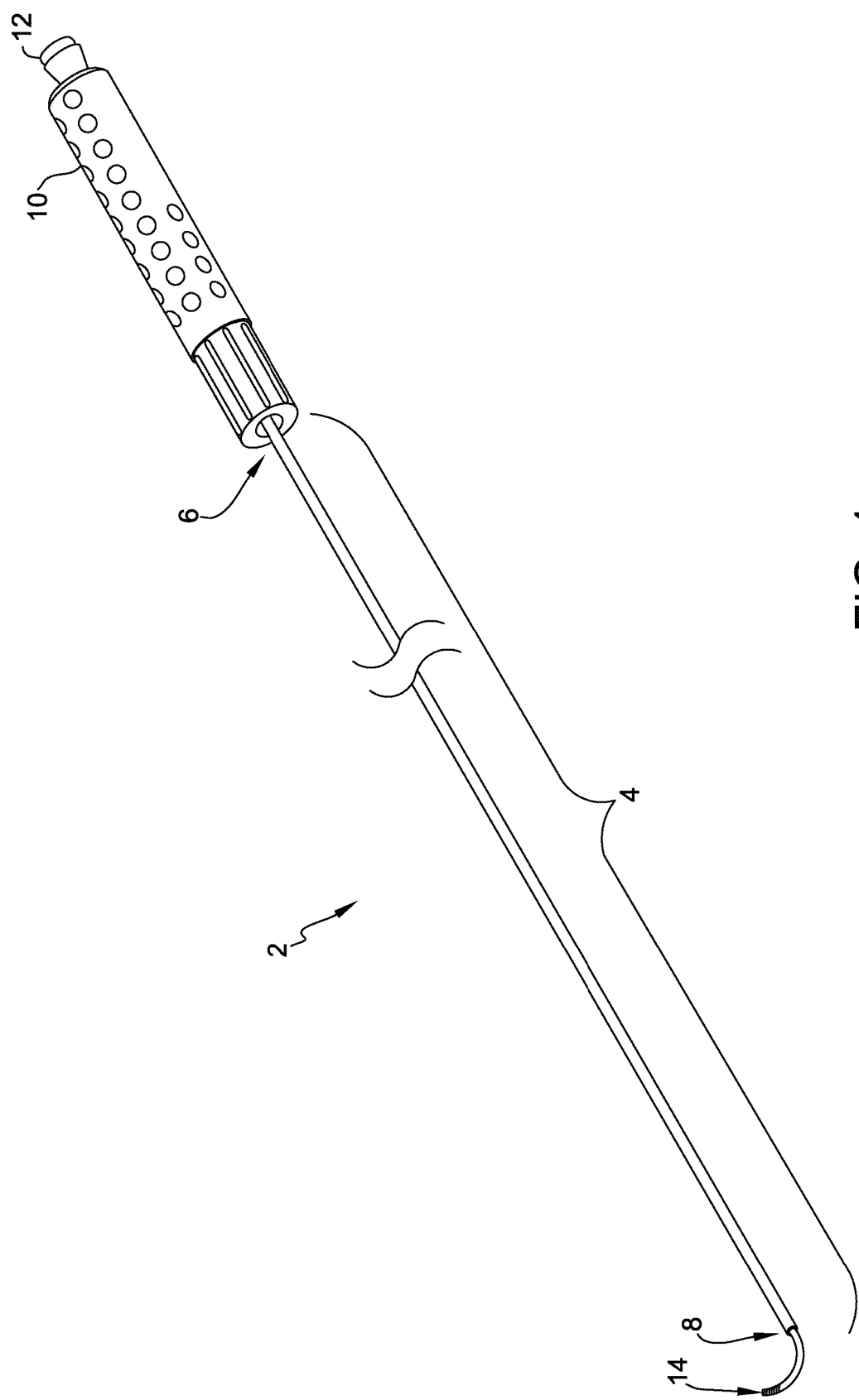
FIG. 1 shows a steerable ablation catheter.

Referring now to FIG. 1, there is illustrated steerable ablation catheter 2 for ablating target tissue of a vessel of the body in accordance with one embodiment of the present disclosure. Although generally described herein in the context of a renal denervation catheter for the ablation of nerves in a vessel wall, steerable ablation catheter 2 may be any suitable ablation catheter conventionally known that may benefit from the rotational monitoring means as described herein. Steerable ablation catheter 2 includes catheter handle 10 and flexible elongate catheter body 4 having proximal end 6 and distal end 8. The length of steerable ablation catheter 2 is generally sufficient to access a target vessel of the body, such as a patient's renal artery, relative to a percutaneous access location. Steerable ablation catheter 2 also includes hub 12 operably connected to an inner lumen (not shown) within catheter handle 10 for insertion or delivery of catheter assemblies and wires as conventionally known. Steerable ablation catheter 2 further includes electrode 14 near distal end 8. Electrode 14 may be a single electrode, or may contain multiple electrodes as is known in the art. Catheter handle 10 is coupled to flexible elongate catheter body 4 such that a torque imparted to catheter handle 10 can be transmitted to flexible elongate catheter body 4, as well as to electrode 14 that is coupled to flexible elongate catheter body 4.

Figure 2:
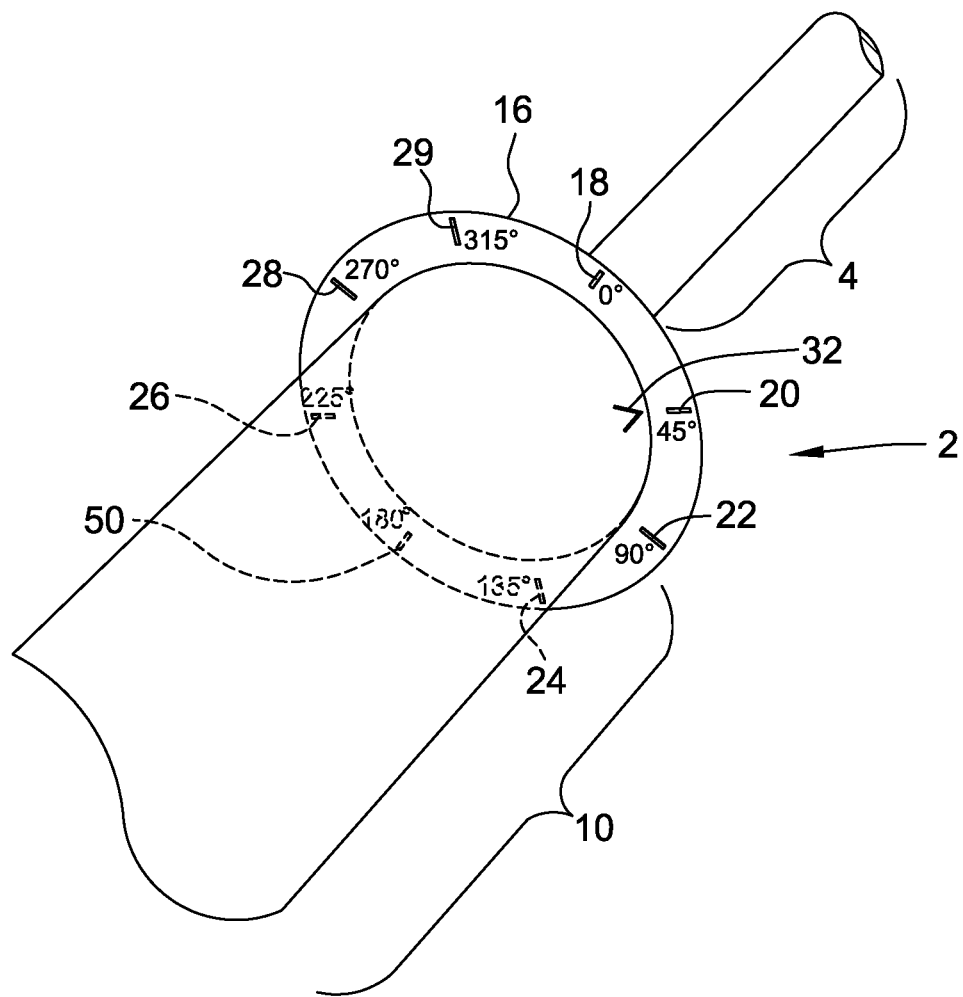
FIG. 2 shows a steerable ablation catheter including rotational monitoring means in accordance with one embodiment of the present disclosure.

Referring now to FIG. 2, there is illustrated a first embodiment of the present disclosure wherein steerable ablation catheter 2 includes flexible elongate catheter body 4, catheter handle 10, and non-rotating rotational monitor 16 including angular markings 18, 20, 22, 24, 26, 28, 29, and 50 for tracking the rotational history of catheter handle 10. Catheter handle 10 further includes rotational angle indicator 32. Non-rotating rotational monitor 16 is mounted to catheter handle 10 such that when catheter handle 10 is rotated during an ablation procedure, catheter handle 10, including rotational angle indicator 32 easily rotates such that electrode 14 directed thereby rotates as well, but non-rotating rotational monitor 16 remains in a fixed, non-moveable position, such that rotational angle indicator 32 can be rotated around non-rotating rotational monitor 16 and its position noted by angular markings 18, 20, 22, 24, 26, 28, 29, and 50. This allows for precise tracking of the rotational history of catheter handle 10, and hence electrode 14 directed thereby, during an ablation procedure.

As noted above, during a renal denervation procedure a doctor will generally ablate multiple segments along and around the artery wall for several seconds to treat the efferent and afferent nerves that typically run the length of the artery. Treating the entire circumferential area of the artery is desirable and, as such, the doctor will typically rotate catheter handle 10 prior to each successive ablation treatment to move electrode 14 circumferentially around the interior of the artery. By including rotational angle indicator 32 on catheter handle 10 of steerable ablation catheter 2, a doctor can easily and accurately determine where, around the circumference of the artery, electrode 14 has traveled and provided ablation such that a more complete and thorough circumferential ablation of the artery can be accomplished during the procedure. For example, prior to any ablation, a doctor may set the rotational angle indicator 32 to the 0 degree angular marking 18 position, and then after a first ablation is made on a renal artery, the doctor may pull electrode 14 along the length of the artery a desired amount and then rotate catheter handle 10 45 degrees until rotational angle indicator 32 shows 45 degrees before a second ablation is done to direct electrode 14 a known amount about the circumference of the artery wall. After the second ablation, the doctor may again pull electrode 14 along the length of the artery a desired amount and then rotate catheter handle 10 another 45 degrees until rotational angle indictor 32 shows 90 degrees before a third ablation is done. This process may be used successively throughout the entire ablation procedure to improve the circumferential ablation history of the procedure. As will be recognized by one of skill in the art, the actual amount of rotation of electrode 14 about the circumference of a vessel wall prior to each ablation may be more or less than 45 degrees without departing from the scope of the present disclosure. Also, each successive amount of rotation of electrode 14 about the circumference of a vessel may be the same or different.

In one specific embodiment using non-rotating rotational monitor 16 as described above, non-rotating rotational monitor 16 is wired or otherwise connected through steerable ablation catheter 2, such that the readings from non-rotating rotational monitor 16 may be transmitted to a visual medium for a doctor to monitor during a procedure. In this specific embodiment, as catheter handle 10 of steerable ablation catheter 2 is rotated during the procedure, the angle of rotation is not only visible on non-rotating rotational monitor 16 using rotational angle indicator 32 as described above, but may also be electronically transmitted to a suitable screen for visualization there as well. The system may also be appropriately configured for audible indications as well.

Figure 3:
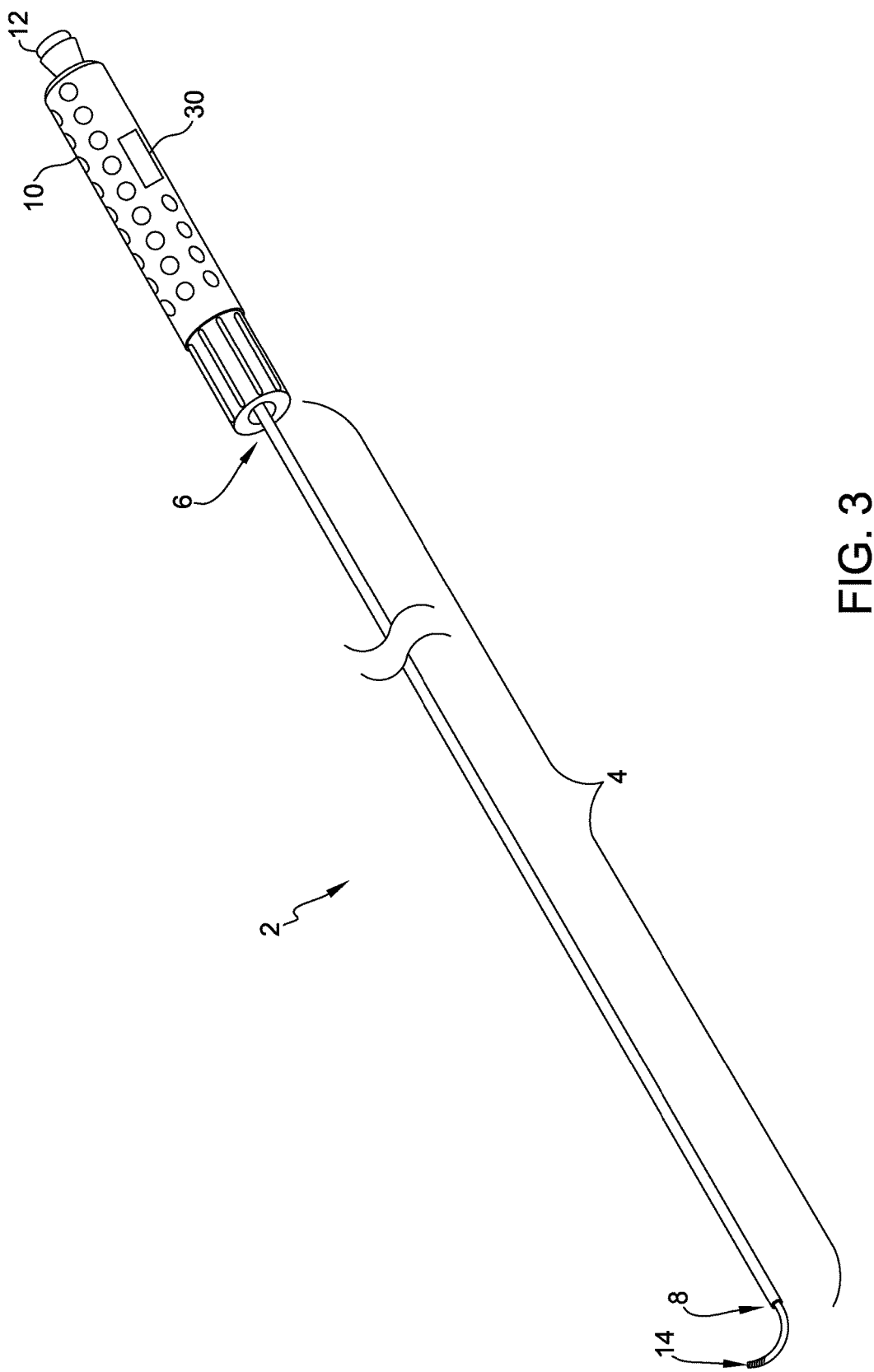
FIG. 3 shows a steerable ablation catheter including rotational monitoring means in accordance with another embodiment of the present disclosure.

Referring now to FIG. 3, there is illustrated steerable ablation catheter 2 for ablating target tissue of a vessel of the body in accordance with another embodiment of the present disclosure. Steerable ablation catheter 2 includes catheter handle 10 and flexible elongate catheter body 4 having proximal end 6 and distal end 8. The length of steerable ablation catheter 2 is generally sufficient to access a target vessel of the body, such as a patient's renal artery, relative to a percutaneous access location. Steerable ablation catheter 2 also includes hub 12 operably connected to an inner lumen (not shown) within catheter handle 10 for insertion or delivery of catheter assemblies and wires. Steerable ablation catheter 2 further includes electrode 14 near distal end 8. Electrode 14 may be a single electrode, or may contain multiple electrodes as is known in the art. Catheter handle 10 is coupled to flexible elongate catheter body 4 such that a torque imparted to catheter handle 10 can be transmitted to flexible elongate catheter body 4, as well as to electrode 14 that is coupled to flexible elongate catheter body 4. Catheter handle 10 additionally includes microelectromechanical systems (MEMS) sensor 30, such as a MEMS sensor chip, which may include analog and/or digital technology for gathering and transmitting data. In one embodiment, the MEMS sensor chip includes a MEMS inertial sensor chip suitable for tracking, recording, and transmitting data related to rotational movement about an axis. Such MEMS inertial sensor chips are known to those of skill in the art.

MEMS sensor 30 is suitably configured and installed onto or near catheter handle 10 to electronically track, record, and transmit the rotational history of catheter handle 10 throughout an ablation procedure such that the rotational history of electrode 14 may also be known. MEMS sensor 30 may suitably be electronically connected and wired through steerable ablation catheter 2 (or may be connected wirelessly) such that the readings from MEMS sensor 30 may be transmitted to a visual medium for a doctor to monitor during a procedure. In this specific embodiment, as catheter handle 10 of steerable ablation catheter 2 is rotated during the procedure, the angle of rotation is electronically tracked, recorded, and transmitted to a suitable screen for visualization by the doctor such that the doctor can more accurately know the ablation history of electrode 14 in the body, and specifically in the artery. The system may also be appropriately configured for audible indications as well.

Figure 4:
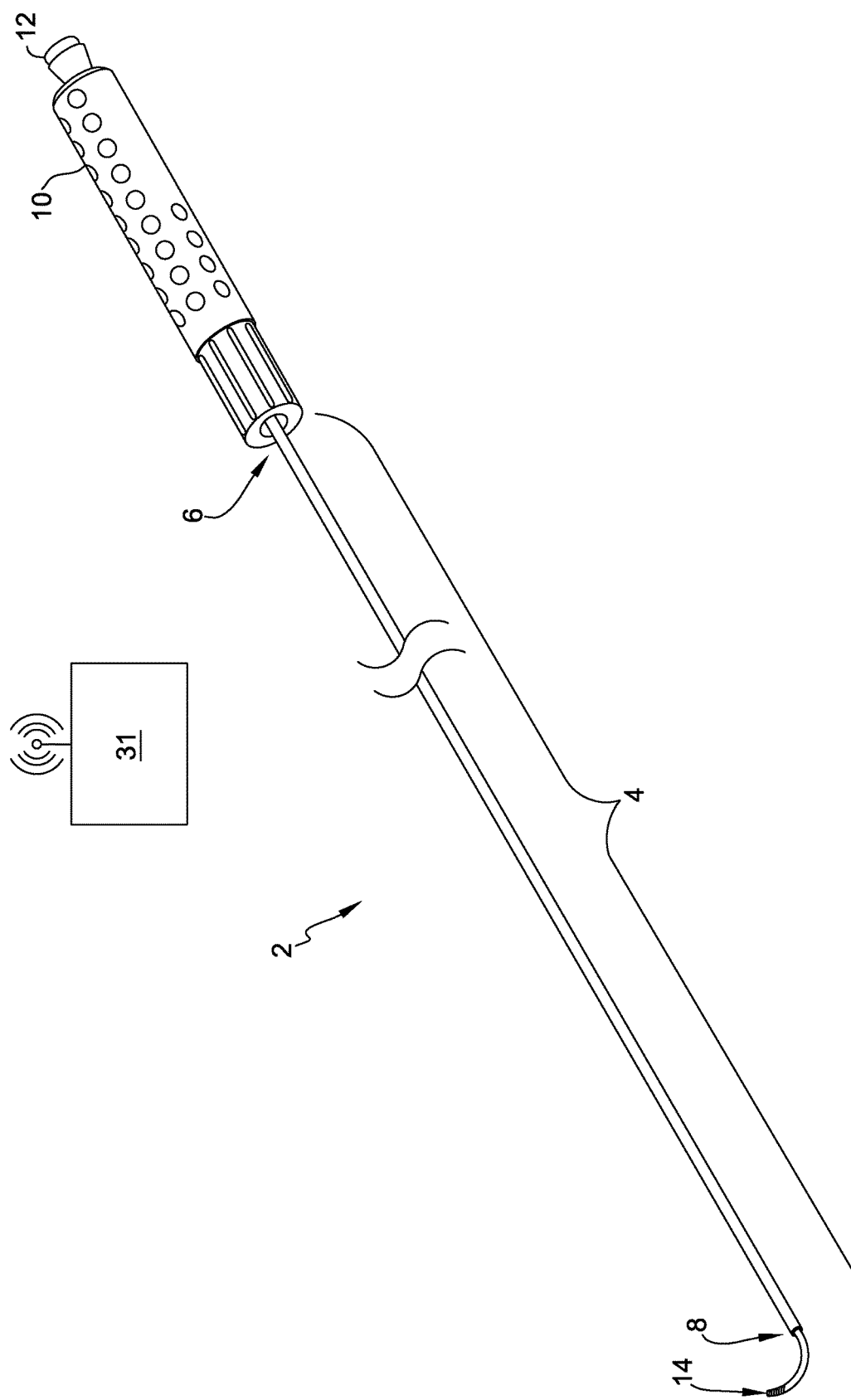
FIG. 4 shows a steerable ablation catheter including rotational monitoring means in accordance with yet another embodiment of the present disclosure.

Referring now to FIG. 4, there is illustrated an ablation catheter system including steerable ablation catheter 2 for ablating target tissue of a vessel of the body in accordance with yet another embodiment of the present disclosure. Steerable ablation catheter 2 includes catheter handle 10 and flexible elongate catheter body 4 having proximal end 6 and distal end 8. The length of steerable ablation catheter 2 is generally sufficient to access a target vessel of the body, such as a patient's renal artery, relative to a percutaneous access location. Steerable ablation catheter 2 also includes hub 12 operably connected to an inner lumen (not shown) within catheter handle 10 for insertion or delivery of catheter assemblies and wires. Steerable ablation catheter 2 further includes electrode 14 near distal end 8. Electrode 14 may be a single electrode, or may contain multiple electrodes as is known in the art. Catheter handle 10 is coupled to flexible elongate catheter body 4 such that a torque imparted to catheter handle 10 can be transmitted to flexible elongate catheter body 4, as well as electrode 14 that is coupled to flexible elongate catheter body 4. The system additionally includes external motion detector 31 that is positioned to monitor, record, and transmit the rotational movement of catheter handle 10 during an ablation procedure. External motion detector 31 may be an analog motion detector or a digital motion detector. Suitable analog and digital motion detectors are known to those of skill in the art.

External motion detector 31 is suitably configured in conjunction with catheter handle 10 to electronically track, record, and transmit the rotational history of catheter handle 10 throughout an ablation procedure such that the rotational history of electrode 14 may also be known. External motion detector 31 may suitably be electronically connected such that the readings from external motion detector 31 are transmitted to a visual medium for a doctor to monitor during a procedure. In this specific embodiment, as catheter handle 10 of steerable ablation catheter 2 is rotated during the procedure, the angle of rotation is electronically tracked, recorded, and transmitted to a suitable screen for visualization by the doctor such that the doctor can more accurately know that ablation history of electrode 14 in the body, and specifically in the artery. The system may also be appropriately configured for audible indications as well. Although illustrated herein as an external motion detector, the present disclosure also contemplates a motion detected coupled directly to the steerable ablation catheter, and specifically on the catheter handle of the steerable ablation catheter.

The means for monitoring the rotational history of catheter handle 10 as set forth herein and specifically including non-rotating rotational monitor 16, MEMS sensor 30, and external motion detector 31, should desirably have an output proportional to the actual rotation angle of electrode 14 directed by catheter handle 10; that is, although the means for monitoring as described herein is monitoring the rotational history of catheter handle 10, the rotational angle output should be for electrode 14 as directed by catheter handle 10. As such, if the torque-ability of catheter handle 10 and electrode 14 is 1:1, the resulting rotational angle should so indicate and would be exactly that of catheter handle 10. If the torque-ability is other than 1:1, the rotational angle indicated should be appropriately calibrated to compensate for the difference to ensure accurate measurements of the circumferential ablation history.

In accordance with the present disclosure, the circumferential rotational history of catheter handle 10, and hence the circumferential ablation history of electrode 14 directed by catheter handle 10 and used to ablate the tissue, can be suitably used by a doctor not only to monitor the circumferential ablation history for an artery or other body area, but can also be used in combination with other information to generate a percent overall circumferential denervation of the of the artery. This can be done in real time during the ablation procedure, which is advantageous as the accuracy and completeness of the procedure can be improved as well as overall patient outcomes.

As noted herein, the present disclosure provides ablation catheters and systems, as well as methods of their use, for recording the rotational history of catheter handle 10, and hence the rotational ablation history of electrode 14 attached to and directed by catheter handle 10 and located within a vessel in the body. This information, along with knowledge of the average ablation spot size and the diameter of the vessel being ablated, may provide acute procedural success information to the doctor as to the overall percent denervation of the renal efferent and afferent nerves of the vessel.

For renal denervation procedures, the average ablation spot size on the vessel has a length of about 2 millimeters to about 5 millimeters, which corresponds generally to an area of about 3 square millimeters to about 20 square millimeters. The average diameter of the vessel is generally about 2 millimeters to about 12 millimeters, including from about 3 millimeters to about 10 millimeters, and including about 4 millimeters to about 8 millimeters. If a doctor knows the diameter of a vessel ($D_v$), the circumference of the vessel ($C_v$) can be calculated. By knowing the average diameter of ablation spots ($D_{as}$) (with respect to the circumference of the vessel), and the number of ablation spots (desirably at least 2, 3, 4, 5, 6, or more), the percent circumferential denervation of the vessel can be estimated using the following equation:

$$\% \text{ Circumferential Denervation}=100\times[[(D_{as1}+D_{as2}+D_{as3}+\ldots)-(O_{ca})]/C_v]$$

wherein $O_{ca}$ is the overlap of circumferential ablation as obtained from the rotational monitor means as described herein. This equation estimates the percent circumferential denervation while accounting for any circumferential overlap of the ablation spots, which is determined by the output of the rotational monitor means.

By allowing a doctor to have an estimation of the percent circumferential denervation of a vessel as calculated in real time during a procedure, the present disclosure allows a doctor to make necessary adjustments during a procedure to improve overall patient outcomes and improves the probability of achieving the desired percent denervation in a single procedure.

Although a number embodiments of this disclosure have been described above with a certain degree of particularity, those skilled in the art could make numerous alterations to the disclosed embodiments without departing from the spirit or scope of the disclosure. For example, an important feature of this disclosure is the rotational monitoring means used in combination with the catheter handle that directs the ablation electrode(s). One skilled in the art may modify the exact nature of the rotational monitoring means without departing from the spirit or scope of the disclosure. It is intended that all matter contained in the above description or shown in the accompanying drawings shall be interpreted as illustrative only and not limiting. Changes in detail or structure may be made without departing from the spirit of the disclosure as defined in the claims.

What is claimed is:

1. A method for monitoring the circumferential ablation history of a renal artery, the method comprising:
    ablating a first area on the renal artery using an ablation system comprising a catheter handle, an elongate catheter body, and an electrode;
    rotating the catheter handle by a first predetermined rotational angle indicated by a means for monitoring an angular rotation of the catheter handle during an ablation procedure, said rotating the catheter handle comprising rotating the electrode by the first predetermined rotational angle;
    recording the first predetermined rotational angle; and
    ablating a second area on the renal artery using the ablation system.

2. The method of claim 1, wherein rotating the catheter handle by a first predetermined angle comprises rotating the catheter handle according to a visual output from a non-rotating rotational monitor.

3. The method of claim 2, wherein rotating the catheter handle according to a visual output from a non-rotating rotational monitor comprises rotating the catheter handle to align a rotational angle indicator on the catheter handle with a first angular marking on the non-rotating rotational monitor.

4. The method of claim 3, wherein rotating the catheter handle to align a rotational angle indicator on the catheter handle with a first angular marking on the non-rotating rotational monitor comprises rotating the catheter handle to align the rotational angle indicator on the catheter handle with the first angular marking proportional to a first predetermined rotation angle of the catheter handle.

5. The method of claim 3, wherein rotating the catheter handle to align a rotational angle indicator on the catheter handle with a first angular marking on the non-rotating rotational monitor comprises rotating the catheter handle to align the rotational angle indicator on the catheter handle with the first angular marking proportional to a first predetermined rotation angle of the electrode.

6. The method of claim 1, wherein rotating the catheter handle by a first predetermined angle comprises rotating the catheter handle according to a visual output from a motion detector.

7. The method of claim 1, wherein rotating the catheter handle by a first predetermined angle comprises rotating the catheter handle by the first predetermined angle proportional to a first predetermined rotational angle of the electrode.

8. An ablation catheter system comprising:
    a rotatable catheter handle comprising a means for monitoring a rotational angle of the catheter handle;
    an elongate catheter body; and
    an electrode configured to rotate with rotational movement of the rotatable catheter handle.

9. The ablation catheter system of claim 8, wherein the means for monitoring the rotational angle of the catheter handle is configured to monitor a rotational angle of the electrode during an ablation procedure.

10. The ablation catheter system of claim 8, wherein the means for monitoring the rotational angle of the catheter handle comprises a non-rotating rotational monitor attached to and circumscribing the catheter handle.

11. The ablation catheter system of claim 10, wherein the non-rotating rotational monitor includes a series of visible markings indicating values for angles.

12. The ablation catheter system of claim 11, wherein the catheter handle further comprises a rotational angle indicator configured to align with one or more visible marking of the series of visible markings.

13. The ablation catheter system of claim 8, wherein the means for monitoring the rotational angle of the catheter handle comprises a motion detector.

14. The ablation catheter system of claim 13, wherein the catheter handle further comprises a screen to display visual output from the motion detector.

15. The ablation catheter system of claim 8, wherein the means for monitoring the rotational angle of the catheter handle comprises a micro-electromechanical system.

16. The ablation catheter system of claim 15, wherein the catheter handle further comprises a screen to display visual output from the micro-electromechanical system.

17. A method for estimating the circumferential percent renal denervation for a renal artery, the method comprising:

initializing an ablation system including an ablation catheter comprising a catheter handle, an elongate catheter body, and an electrode;

ablating a first area on the renal artery using the ablation system;

rotating the catheter handle by a first predetermined rotational angle indicated by a means for monitoring an angular rotation of the catheter handle during an ablation procedure, wherein said rotating the catheter handle also rotates the electrode by the first predetermined rotational angle;

recording the first predetermined rotational angle;

ablating a second area on the renal artery using the ablation system; and using an average ablation spot size, a diameter of the artery, and circumferential angle for each ablation to estimate the circumferential percent renal denervation for the artery.

18. The method of claim 17, wherein rotating the catheter handle by a first predetermined angle comprises rotating the catheter handle by the first predetermined angle proportional to a first predetermined rotational angle of the electrode.

19. The method of claim 17, wherein rotating the catheter handle by a first predetermined angle comprises rotating the catheter handle by the first predetermined angle proportional to a first predetermined rotational angle of the catheter handle.

20. The method of claim 1, wherein rotating the catheter handle by a first predetermined angle comprises rotating the catheter handle according to a visual output from at least one of a non-rotating rotational monitor and a motion detector.

* * * * *